US00PP35932P2

(12) United States Plant Patent
Salmon

(10) Patent No.: US PP35,932 P2
(45) Date of Patent: Jul. 2, 2024

(54) ***ALLIUM* PLANT NAMED 'FB2020'**

(50) Latin Name: *Allium nutans*
Varietal Denomination: FB2020

(71) Applicant: AD Salmon and BM Thomas, Gapsted (AU)

(72) Inventor: Alexander Salmon, Gapsted (AU)

(73) Assignee: Ad Salmon and BM Thomas (AU)

( * ) Notice: Subject to any disclaimer, the term of this patent is extended or adjusted under 35 U.S.C. 154(b) by 0 days.

(21) Appl. No.: 18/382,537

(22) Filed: Oct. 23, 2023

(51) Int. Cl.
*A01H 5/02* (2018.01)
*A01H 6/04* (2018.01)

(52) U.S. Cl.
USPC ..... Plt./263.1

(58) Field of Classification Search
USPC ..... Plt./263.1
See application file for complete search history.

*Primary Examiner* — Karen M Redden
(74) *Attorney, Agent, or Firm* — Cassandra Bright

(57) ABSTRACT

A new and distinct *Allium* cultivar named 'FB2020' is disclosed, characterized by foliage having a grey-green glaucous layer. Flowers are purple. The new variety is an *Allium*, typically produced as an outdoor ornamental plant.

2 Drawing Sheets

Latin name of the genus and species: *Allium nutans.*
Variety denomination: 'FB2020'.

BACKGROUND OF THE INVENTION

The new cultivar is the product of chance discovery. The new variety originated as a naturally occurring whole plant mutation of the unpatented 'Cobalt Millennium' variety of *Allium*. The new variety was selected by the inventor, during February of 2017, at a commercial nursery in Victoria, Australia.

Asexual reproduction of the new cultivar 'FB2020' was first performed by division in Victoria, Australia in February of 2017. The new variety was maintained as a separate clone and tested for performance and stability over 5 generations. During the evaluation period, access to all plants was restricted, as plants were kept in a location not open to the public. Through subsequent propagation, multiple generations have been reproduced, which have shown that the unique features of this cultivar are stable and reproduced true to type.

Date of first sale was Oct. 31, 2022, in Australia. This sale was made directly by the inventor or one who obtained the claimed invention directly or indirectly from the inventor. This sale and all public disclosures made between Oct. 31, 2022 and the filing of this application fall within the exception allowed under 102(b)(1).

SUMMARY OF THE INVENTION

The cultivar 'FB2020' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FB2020'. These characteristics in combination distinguish 'FB2020' as a new and distinct *Allium* cultivar:

1. Grey-green glaucous foliage.
2. Purple flowers.

PARENT COMPARISON

Plants of the new cultivar 'FB2020' are similar to the parent, *Allium* 'Millenium Cobalt' in most horticultural characteristics. The new variety, however, differs in the following ways:

1. The new variety produces grey-green glaucous foliage, compared to the green foliage of parent.

COMMERCIAL COMPARISON

Plants of the new cultivar 'FB2020' are similar to the commercial variety *Allium* 'Pink Pepper', unpatented, in most horticultural characteristics. The new variety, however, differs in the following:

1. 'FB2020' has a purple flower; flowers of 'Pink Pepper' are pink.
2. 'FB2020' has grey/green foliage; foliage of 'Pink Pepper' is green.

BRIEF DESCRIPTION OF THE PHOTOGRAPHS

Figure 1:
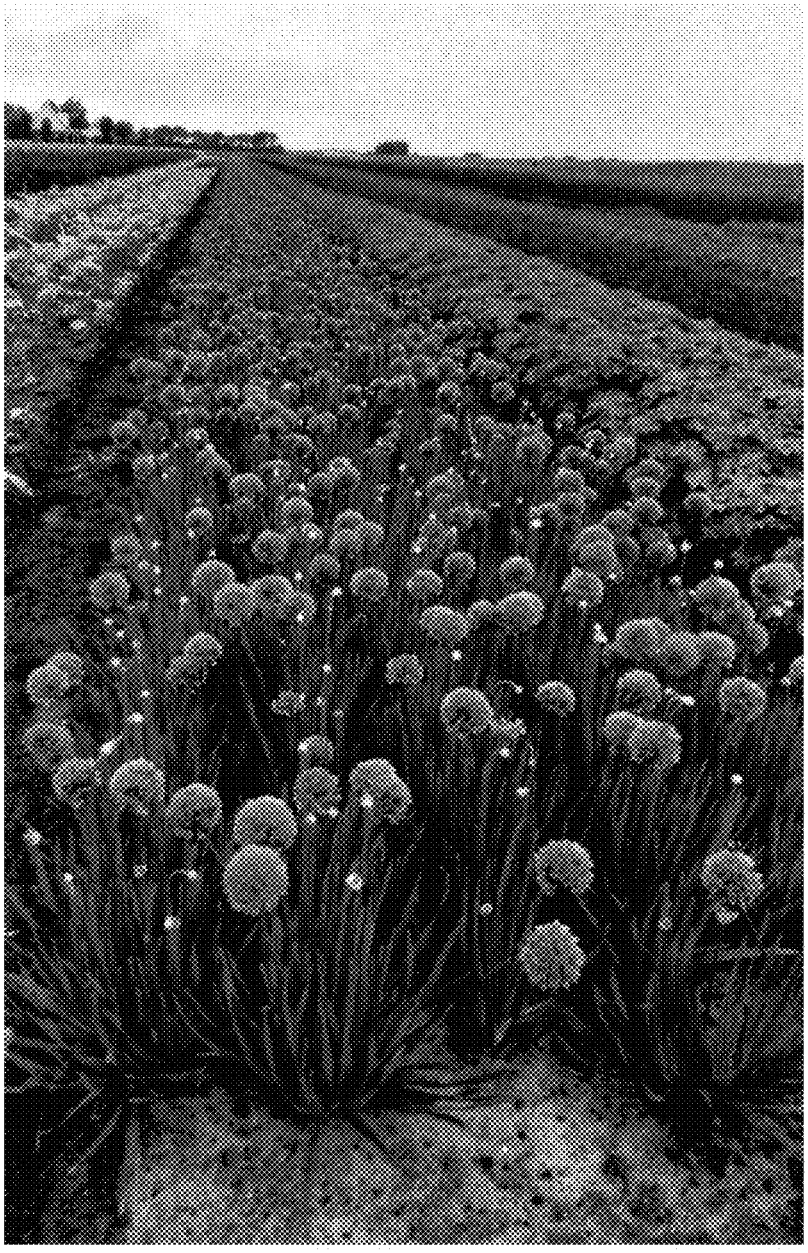

The accompanying photograph in FIG. 1 illustrates in full color a typical plants of 'FB2020' at approximately 22 months old from a rooted cutting grown in Victoria, Australia.

Figure 2:
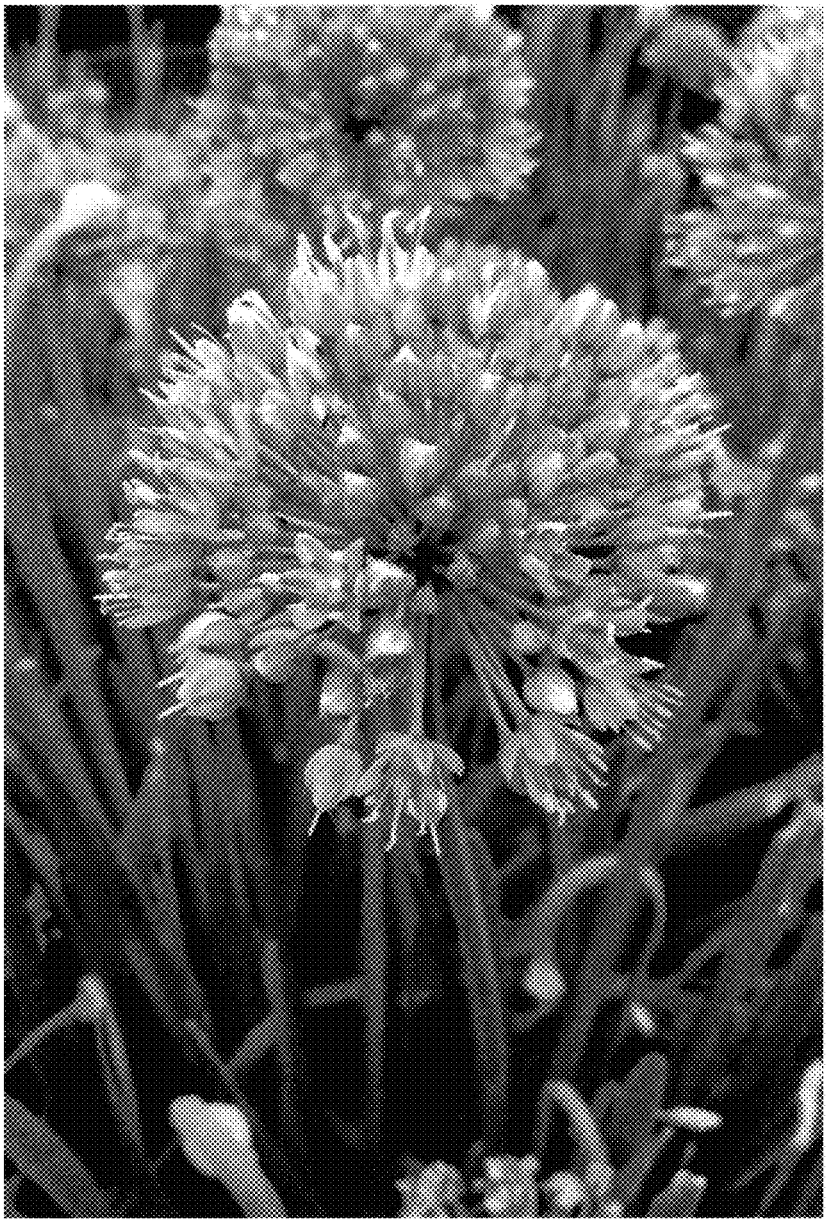

FIG. 2 illustrates in full color a close up of the flowers of 'FB2020'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'FB2020' plants grown outdoors in Victoria, Australia. Plants are 660 days old from division, 420 days from potting. Temperatures ranged from approximately 5° C. to 15° C. at night and 10° C. to 32° C. during the day. No artificial light, photoperiodic treatments were given to the plants. No chemical treatments were given to plants. Measurements and numerical values represent averages of typical plant types.

Botanical classification: *Allium nutans* 'FB2020'.

ROOTS

Root description: Moderately, fleshy root system colored near Brown 199D and Orange-White 159C. No rhizomes.

PLANT

Growth habit: Clump forming tender perennial with upright foliage.

Height: Foliar plane 25 to 30 cm. Flowering plane 34.5 cm.

Plant spread: Approximately 30.5 cm.

Growth rate: Moderate, slower growth than non-variegated forms.

Growth pattern: Sessile rosulate foliage with no stem.

FOLIAGE

Leaf:

*Average leaf length*.—Approximately 20 to 25 cm.

*Average leaf width*.—Approximately 0.7 cm.

*Arrangement*.—Basal, irregular whorls.

*Shape of blade*.—Linear.

*Apex*.—Acute.

*Margin*.—Entire.

*Texture of top surface*.—Smooth.

*Texture of bottom surface*.—Smooth.

*Quantity of leaves per plant*.—Average 144 on a mature plant of 22 months old.

*Color*.—Mature Upper surface: Near Green 138A, with a strong glaucous overlay near Greyed-Green 189A. Mature Lower surface: Near Green 138A, with a strong glaucous overlay near Greyed-Green 189A.

*Base*.—Truncate, non-clasping.

*Aspect*.—Upright.

FLOWER

Natural flowering season: Begins flowering in Spring in Australia. Flowering season goes to late summer.

Inflorescence type: Terminal Umbel with approximately 150 to 180 flowers per umbel.

Individual flower type: Single.

Flower profile: Funnelform.

Lasting quality: Inflorescence shows no significant signs of aging for approximately 5 to 6 weeks.

Bud:

*Shape*.—Narrow ovate.

*Length*.—Approximately 0.6 cm.

*Diameter*.—Approximately 0.4 cm.

*Color*.—Near RHS Purple 77B.

Umbel size:

*Diameter*.—Average 5.4 cm.

*Height*.—Average 3.0 cm.

Corolla:

*Arrangement*.—Apetalous, single, campanulate flowers composed of 6 basally fused tepals, shaped into a flared trumpet.

*Size*.—Length: Approximately 1.1 cm. Width: Approximately 0.8 cm at widest point. Lobe Length: Approximately 0.8 cm. Lobe Width: Average 0.3 cm.

*Margin*.—Entire.

*Shape*.—Lanceolate.

*Apex*.—Broadly acute.

*Texture*.—Glabrous all surfaces.

Color:

*Tepals*.—Outer surface: Near Purple 77B. Inner surface: Near Purple 77B.

*Sepals*.—Not Present.

Fragrance: None.

Flower filament color: Near Purple 77D.

Flower anther color: Near Purple 75D.

Anther quantity: 6, each approximately 0.2 cm long.

Stamen protrusion: Yes.

Pollen: Not observed.

Pistil:

*Number*.—1.

*Length*.—Approximately 0.9 cm.

*Stigma*.—Shape: Linear. Color: Near Purple 76C.

Flower style color: Near Purple 76D.

Peduncle:

*Length*.—Average 25 cm.

*Diameter*.—0.5 cm.

*Texture*.—Glabrous, glaucous ribbed.

*Color*.—Near Green 138B, heavily flushed Greyed-Green 189A.

Pedicel:

*Length*.—1.5 cm.

*Diameter*.—About 1 mm.

*Texture*.—Glabrous.

*Color*.—Near Green 138B, heavily flushed Greyed-Green 189A.

Fragrance: None.

OTHER CHARACTERISTICS

Seed production: No seed produced to date.

Disease resistance: Seems unaffected by any disease.

Temperature tolerance: Not tested but expected to handle −5° C. to +30° C.

Drought tolerance: Will tolerate considerable dryness once established.

What is claimed is:

1. A new and distinct cultivar of *Allium* plant named 'FB2020' as herein illustrated and described.

* * * * *